US012773376B2

(12) United States Patent
Nakashima et al.

(10) Patent No.: US 12,773,376 B2
(45) Date of Patent: Oct. 27, 2026

(54) DENTAL IMPRESSION MATERIAL AND COMBINATION IMPRESSION MATERIAL

(71) Applicant: GC Corporation, Shizuoka (JP)

(72) Inventors: Yusuke Nakashima, Tokyo (JP); Naofumi Niizeki, Tokyo (JP)

(73) Assignee: GC Corporation, Shizuoka (JP)

( * ) Notice: Subject to any disclaimer, the term of this patent is extended or adjusted under 35 U.S.C. 154(b) by 857 days.

(21) Appl. No.: 17/757,488

(22) PCT Filed: Oct. 23, 2020

(86) PCT No.: PCT/JP2020/039939

§ 371 (c)(1),
(2) Date: Jun. 16, 2022

(87) PCT Pub. No.: WO2021/131291

PCT Pub. Date: Jul. 1, 2021

(65) Prior Publication Data

US 2023/0016218 A1 Jan. 19, 2023

(30) Foreign Application Priority Data

Dec. 26, 2019 (JP) ................................ 2019-237346

(51) Int. Cl.
*A61K 6/90* (2020.01)
*A61C 9/00* (2006.01)

(52) U.S. Cl.
CPC .............. *A61K 6/90* (2020.01); *A61C 9/0006* (2013.01)

(58) Field of Classification Search
None
See application file for complete search history.

(56) References Cited

U.S. PATENT DOCUMENTS 4,060,421 A 11/1977 Yoshikawa et al.
2006/0120210 A1 * 6/2006 Kamohara ........... A61C 9/0026 366/79
2006/0213396 A1 9/2006 Kamohara et al.
2013/0032058 A1 2/2013 Gyakushi et al.
2013/0220172 A1 * 8/2013 Nagasawa ................ A61K 6/90 106/35
2014/0228473 A1 * 8/2014 Osswald ................ A61K 6/887 526/279
2019/0076336 A1 3/2019 Usuki et al.

FOREIGN PATENT DOCUMENTS

| | | |
|---|---|---|
| CN | 102811696 | 12/2012 |
| EP | 1707178 | 10/2006 |
| EP | 2561852 | 2/2013 |
| JP | S56-020019 | 5/1981 |
| JP | H05-017315 | 1/1993 |
| JP | 2006-273720 | 10/2006 |
| JP | 5559904 | 7/2014 |
| JP | 2014-172891 | 9/2014 |
| WO | 2012/063618 | 5/2012 |
| WO | 2017/163491 | 9/2017 |

OTHER PUBLICATIONS

Machine Translation for Sankin (Year: 1993).*
Inoue et al.("Consistency of alginate impression materials and their evaluation", J Oral Rehab., vol. 26, Issue 3, (2001), pp. 203-207) (Year: 2001).*
International Search Report for PCT/JP2020/039939 mailed on Dec. 28, 2020.

* cited by examiner

*Primary Examiner* — Michael Forrest
(74) *Attorney, Agent, or Firm* — IPUSA, PLLC

(57) ABSTRACT

A dental impression material for use in a combination impression method includes a base material paste containing an alginate and water, a gelling agent, and a curing material paste containing a water-insoluble liquid compound, wherein a consistency of a kneaded material formed of the base material paste and the curing material paste is 36 mm or more, and a compressive strength of a cured body is 0.35 MPa or more.

4 Claims, No Drawings

DENTAL IMPRESSION MATERIAL AND COMBINATION IMPRESSION MATERIAL

TECHNICAL FIELD

The present invention relates to a dental impression material and a combination impression material.

BACKGROUND ART

In dental practice, combination impression methods are used to obtain oral impressions when making prostheses.

In the combination impression method, a high fluidity first impression material is first applied to a patient's teeth, and is then followed by applying a low fluidity second impression material. Thus, the first impression material and the second impression material are bonded together to obtain a highly accurate oral impression.

Conventionally, the agar-alginate combination impression method is known as the combination impression method (see, for example, Patent Document 1). The agar-alginate combination impression method uses a high fluidity agar impression material and a low fluidity alginate impression material as the combination impression material.

PRIOR ART DOCUMENTS

Patent Documents

Patent Document 1: Japanese Unexamined Patent Publication No. S56-20019

SUMMARY OF INVENTION

Problem to be Solved by the Invention

However, there has been a problem that complicated operations such as heat melting, heat insulation, temperature adjustment, and the like are indispensable, and the handleability is low, because the fluidity of the agar impression material depends on temperature.

One aspect of the present invention is to provide a dental impression material having excellent handleability and capable of obtaining a highly accurate impression even when the impression material is used with an alginate impression material.

Means for Solving Problems

One aspect of the present invention is to provide a dental impression material for use in a combination impression method, the dental impression material includes a base material paste containing an alginate and water, and a curing material paste containing a gelling agent and a water-insoluble liquid compound, wherein a consistency of a kneaded material of the base material paste and the curing material paste is 36 mm or more, and wherein a compressive strength of a cured body is 0.35 MPa or more.

Effects of the Invention

According to one aspect of the present invention, the present invention can provide a dental impression material having excellent handleability and capable of obtaining a highly accurate impression even when the dental impression material is used in combination with an alginate impression material.

MODE FOR CARRYING OUT THE INVENTION

Next, an embodiment for carrying out the present invention will be described.

[Dental Impression Material]

The dental impression material of the present embodiment is used in a combination impression method. For example, a dental impression material of the present embodiment may be used in combination with an alginate impression material.

The dental impression material of the present embodiment includes a base material paste containing an alginate and water, and a curing material paste containing a gelling agent and a water-insoluble liquid compound. Therefore, the dental impression material of the present embodiment is excellent in handleability.

A consistency of a kneaded material of the base material paste and the curing material paste is 36 mm or more and preferably 38 mm or more. When the consistency of the kneaded material of the base material paste and the curing material paste is 36 mm or more, the fluidity of the kneaded material of the base material paste and the curing material paste is increased. Therefore, when the dental impression material of the present embodiment is used with the alginate impression material, the accuracy of the impression is improved.

The upper limit of the consistency of the kneaded material of the base material paste and the curing material paste is not particularly limited, but normally 50 mm.

The method of measuring the consistency of the kneaded material of the base material paste and the curing material paste is as follows. The base material paste and the curing material paste are kneaded under conditions of 23° C.±2° C. by manual kneading until the kneaded material becomes homogeneous, and the 0.5±0.2 ml of the kneaded material is placed on a glass plate. Then, 30 seconds after starting the kneading of the base material paste and the curing material paste, weights are placed on the glass plate so that the combined weight of the glass plate the kneaded material become 500 g. The weights are then removed 5 seconds after the weights are loaded, and sizes of the largest and smallest portions between the parallel cuts of the widened kneaded material are measured in units of 0.5 mm. Next, an average of the sizes of the largest and smallest portions between the parallel cuts of the widened kneaded material is determined to be the consistency of the paste.

The compressive strength of the cured body of the dental impression material of the present embodiment is preferably 0.35 MPa or more and 0.50 MPa or more. If the compressive strength of the cured body of the dental impression material is less than 0.35 MPa, when the dental impression material of the present embodiment is used with the alginate impression material, the impression is easily damaged.

The upper limit of the compressive strength of the cured body of the dental impression material in the present embodiment is not particularly limited, but is normally 1.5 MPa.

A Strain-in-compression of the cured body of the dental impression material in the present embodiment is preferably 20% or less and further preferably 18% or less. If the Strain-in-compression of the cured body of the dental impression material of the present embodiment is 20% or less, a size stability of the cured body of the dental impression material in the present embodiment is improved. Therefore, when the dental impression material of the present embodiment is used with the alginate impression material, the accuracy of the impression is improved.

The lower limit of Strain-in-compression of the cured body of the dental impression material in the present embodiment is not particularly limited, but is normally 10%.

The cured body of the dental impression material in the present embodiment is prepared by mixing the base material paste and the curing material paste with a mass ratio of 2:1 in accordance with JIS 6505:2005, 6.6.2 and then curing for 90 seconds.

The initial cure time of the dental impression material in the present embodiment is preferably 30 to 240 seconds and even more preferably 50 to 120 seconds.

[Base Material Paste]

The base material paste includes an alginate and water.

Examples of the alginates include alkali metal salts of alginates such as sodium alginate, potassium alginate, and the like; and ammonium salts of alginates such as ammonium alginate, triethanolamine alginate, and the like. Two or more kinds of alginates may be used in combination. Among these, from the viewpoint of accessibility, ease of handling, and physical properties of the cured body of the dental impression material in the present embodiment, the alkali metal salt of alginate is preferably used, and the potassium alginate is further preferably used.

The viscosity of 1% by mass of aqueous alginate solution at 20° C. is preferably in the range of 100 to 400 mPa·s, and more preferably in the range of 100 to 200 mPa·s. If the viscosity of 1% by mass of aqueous alginate solution at 20° C. is 100 mPa·s or more, an impression is less likely damaged when the dental impression material of the present embodiment is used with the alginate impression material. On the other hand, if the viscosity of 1% by mass of aqueous alginate solution at 20° C. is 400 mPa·s or less, the fluidity of the kneaded material of the base material paste and the curing material paste is increased. Therefore, when the dental impression material of the present embodiment is used with the alginate impression material, the accuracy of the impression is improved.

The content of the alginate in the base material paste is preferably 1 to 20% by mass, and further preferably 5 to 10% by mass. When the content of the alginate in the base material paste is 1% by mass or more, the impression is not easily damaged when the dental impression material of the present embodiment is used with the alginate impression material. On the other hand, when the content of the alginate in the base material paste is 20% by mass or less, the accuracy of the impression is improved when the dental impression material of the present embodiment is used with the alginate impression material.

The content of the alginate in the dental impression material of the present embodiment is preferably 0.25 to 10% by mass, and further preferably 2 to 8% by mass. If the content of the alginate in the dental impression material of the present embodiment is 0.25% by mass or more, the impression is not easily damaged when the dental impression material of the present embodiment is used with the alginate impression material. On the other hand, if the content of the alginate in the dental impression material of the present embodiment is 10% by mass or less, the accuracy of the impression is improved when the dental impression material of the present embodiment is used with the alginate impression material.

As water, for example, ion-exchanged water, distilled water, or the like may be used, and water sterilized by sodium hypochlorite or the like may be used.

The water content in the base material paste is preferably 80 to 99% by mass and further preferably 90 to 95% by mass.

The water content in the dental impression material in the present embodiment is preferably 40 to 90% by mass, and further preferably 55 to 80% by mass.

The base material paste further preferably contains a curing retarder and the like. This increases the working time of the dental impression material in the present embodiment.

Examples of the curing retarders include a phosphate such as trisodium phosphate, tripotassium phosphate, and the like; a condensed phosphate such as sodium pyrophosphate, potassium pyrophosphate, and the like; and two or more kinds of curing retarders may be used in combination.

The content of the curing retarder in the base material paste is preferably 0.01 to 10% by mass. If the content of the curing retarder in the base material paste is 0.01% by mass or more, the working time of the dental impression material in the present embodiment is increased. If the content of the curing retarder in the base material paste is 10% by mass or less, the initial setting time of the dental impression material in the present embodiment is decreased, and the strength of the cured body of the dental impression material in the present embodiment is improved.

The base material paste may further include fillers, colorants, preservatives, disinfectants, perfumes, pH adjusting agents, surfactants, and the like.

The consistency of the base material paste is preferably 30 mm or more. If the consistency of the base material paste is 30 mm or more, the fluidity of the kneaded material of the base material paste and the curing material paste is increased. Therefore, when the dental impression material of the present embodiment is used with the alginate impression material, the accuracy of the impression is improved.

[Curing Material Paste]

The curing material paste contains a gelling agent and a water-insoluble liquid compound.

As the gelling agent, a compound of a metal with a valence of two or more may be used.

Examples of the compounds of the metal with a valence of two or more include salts, oxides, hydroxides, and the like of metals with a valence of two or more, and two or more kinds of compounds of the metal with a valence of two or more may be used in combination.

Examples of the metal with a valence of two or more include calcium, magnesium, zinc, aluminum, iron, titanium, zirconium, tin, and the like.

Examples of the metal salts with a valence of two or more include calcium sulfate dihydrate ($CaSO_4 \cdot 2H_2O$), calcium sulfate hemihydrate ($CaSO_4 \cdot 1/2H_2O$), anhydrous calcium sulfate ($CaSO_4$), and the like.

Examples of the metal oxides with a valence of two or more include calcium oxide, magnesium oxide, zinc oxide, titanium oxide, zirconium oxide, tin oxide, and the like.

Examples of the metal hydroxides with a valence of two or more include calcium hydroxide, magnesium hydroxide, zinc hydroxide, aluminum hydroxide, iron hydroxide, and the like.

The content of the gelling agent in the curing material paste is preferably 10 to 60% by mass. If the content of the gelling agent in the curing material paste is 10% by mass or more, the strength of the cured body of the dental impression material in the present embodiment is improved. If the content of the gelling agent in the curing material paste is 60% by mass or less, the working time of the dental impression material of the present embodiment is increased.

The water-insoluble liquid compound is not particularly limited as long as the gelling agent can be made into a paste. Examples of the water-insoluble liquid compounds include a hydrocarbon compound, aliphatic alcohol, aromatic alcohol, fatty acid, fatty acid ester, silicone oil, or the like. Two or more of the water-insoluble liquid compounds may be used in combination.

As used herein and in the claims, "water-insoluble" refers to a solubility of 5 g or less in 100 g of water at 20° C.

The hydrocarbon compound can be either a chain compound or a ring compound.

Examples of the hydrocarbon compounds include hexane, heptane, octane, nonane, decane, undecane, dodecane, tridecane, tetradecane, pentadecane, 2,7-dimethyl octane, 1-octene, cycloheptane, cyclononane, kerosene, liquid paraffin, and the like.

The aliphatic alcohol can be either a saturated aliphatic alcohol or an unsaturated aliphatic alcohol.

Examples of the aliphatic alcohols include 1-hexanol, 1-octanol, citronellol, oleyl alcohol, and the like.

Examples of the aromatic alcohols include benzyl alcohol, m-cresol, and the like.

The fatty acids may be either saturated fatty acids or unsaturated fatty acids.

Examples of the fatty acids include hexanoic acid, octanoic acid, oleic acid, linoleic acid, and the like.

The fatty acid esters can be either saturated fatty acid esters or unsaturated fatty acid esters.

Examples of the fatty acid esters include ethyl octanoate, butyl phthalate, glyceride oleate, olive oil, sesame oil, liver oil, whale oil, and the like.

Examples of the silicone oils include polydimethylsiloxanes, polymethylphenylsiloxanes, polymethylhydrogensiloxanes, polyphenylhydrogensiloxanes, and the like.

The content of the water-insoluble liquid compound in the curing material paste is preferably 10 to 50% by mass, and further preferably 15 to 30% by mass. If the content of the water-insoluble liquid compound in the curing material paste is 10% by mass or more, the handleability of the dental impression material of the present embodiment is improved. If the content of the water-insoluble liquid compound in the curing material paste is 50% by mass or less, the strength of the cured body of the dental impression material of the present embodiment is improved.

The curing material paste further preferably contains polybutene. Accordingly, the curability of the dental impression material of the present embodiment is improved, and the working time of the dental impression material of the present embodiment is increased.

The polybutene is preferably liquid.

Polybutene can be synthesized by copolymerizing isobutene with 1-butene.

The number average molecular weight of the polybutene is 300 to 4,000.

The content of the polybutene in the curing material paste is preferably 0.5 to 30% by mass and further preferably 1 to 20% by mass. if the content of the polybutene in the curing material paste is 0.5% by mass or more and 30% by mass or less, the handleability of the dental impression material of the present embodiment is improved.

The curing material paste further preferably contains a curing retarder. This increases the working time of the dental impression material in the present embodiment.

Examples of the curing retarders include phosphate such as trisodium phosphate, tripotassium phosphate, and the like; condensed phosphates such as sodium pyrophosphate, potassium pyrophosphate, and the like; and two or more curing retarders may be used in combination.

The content of the curing retarder in the curing material paste is preferably 0.01 to 10% by mass. If the content of the curing retarder in the curing material paste is 0.01% by mass or more, the working time of the dental impression material of the present embodiment is increased. If the content of the curing retarder in the curing material paste is 10% by mass or less, the initial setting time of the dental impression material of the present embodiment is decreased, and the strength of the cured body of the dental impression material in the present embodiment is improved.

The curing material paste may further contain fillers, curing modifiers, surfactants, colorants, preservatives, disinfectants, flavoring agents, pH modifiers, and the like.

Examples of the materials constituting the filler include clay minerals such as diatomaceous earth, talc, smectite, and the like; inorganic oxides such as silica, alumina, and the like; and two or more materials may be used in combination.

Examples of the curing agent modifiers include potassium titanium fluoride and potassium silicofluoride, and two or more curing agent modifiers may be used in combination.

Examples of the surfactants include polyoxyethylene alkyl ethers and the like, and two or more surfactants may be used in combination.

The consistency of the curing material paste is preferably 30 mm or more. If the consistency of the curing material paste is 30 mm or more, the fluidity of the kneaded material of the base material paste and the curing material paste is increased. Therefore, when the dental impression material of the present embodiment is used with the alginate impression material, the accuracy of the impression is improved.

[Method of Using Dental Impression Materials]

The dental impression material of the present embodiment is used by kneading the base material paste with the curing material paste.

For example, using manual or electric extrusion equipment, the base material paste and the curing material paste, that are filled in a divided packaging container, are extruded, and the kneaded material is applied to teeth by passing through a nozzle.

Examples of the packaging containers include resin or metal molded products, resin or metal bags, and the like.

The mass ratio of the base material paste to the curing material paste is preferably 1 to 5 when the curing material paste is kneaded with the base material paste.

[Combination impression Material]

The combination impression material of the present embodiment includes a dental impression material of the present embodiment and an alginate impression material.

The alginate impression material is not particularly limited. For example, the alginate impression material used in the agar-alginate combination impression method may be used.

The alginate impression material may be a powder or a paste having a curing material paste containing: a base material paste containing an alginate and water; a gelling agent; and a water-insoluble liquid compound.

Here, the paste alginate impression material is similar to the dental impression material of the present embodiment, except that the consistency of the kneaded material of the base material paste and the curing material paste is less than 36 mm.

The combination impression material of the present embodiment can be used to obtain the impression of teeth.

For example, the dental impression material of the present embodiment is applied to the teeth, followed by applying the alginate impression material to the teeth to which the dental impression material of the present embodiment is applied.

EXAMPLES

Hereinafter, examples of the present invention will be described, but the present invention is not limited to examples.

[Preparation of Curing Material Paste for Dental Impression Material]

A curing material paste having a predetermined consistency (see Table 1) was obtained by mixing 45 parts by mass of anhydrous calcium sulfate ($CaSO_4$), 6 parts by mass of magnesium hydroxide, 2 parts by mass of zinc oxide, 23 parts by mass of liquid paraffin, 4 parts by mass of polybutene, 1.5 parts by mass of tripotassium phosphate, 12.5 parts by mass of silica, 3 parts by mass of titanium fluoride, and 3 parts by mass of polyoxyethylene alkyl ether.

[Preparation of Base Material Paste for Dental Impression Material]

The alkali metal salts of alginic acid, water, and sodium pyrophosphate were mixed as indicated in Table 1 [parts by mass] to obtain a base material paste having a predetermined consistency (see Table 1).

The alkali metal salts of alginic acid are described in detail below.

K-1G: potassium alginate K-1G (manufactured by KIMICA Corporation); viscosity of 100 to 200 mPa·s K-3G: potassium alginate K-3G (manufactured by KIMICA Corporation); viscosity of 300 to 400 mPa·s K-1: potassium alginate K-1 (manufactured by KIMICA Corporation); viscosity of 100 to 200 mPa·s K-3: potassium alginate K-3 (manufactured by KIMICA Corporation); viscosity of 300 to 400 mPa·s I-8: Sodium alginate I-8 (manufactured by KIMICA Corporation); viscosity of 800 to 900 mPa·s Here, the viscosity of the alkali metal salt of alginic acid is the viscosity at a 1% by mass aqueous solution of the alkali metal salt of alginic acid at 20° C.

[Consistency of Paste]

Under the conditions of 23° C.±2° C., 0.5±0.2 ml of paste was placed on a glass plate, and then weights were placed so that the total weight of the kneaded material and the glass plate became 500 g. Five seconds after the weights were placed, the weights were removed and the sizes of the largest and smallest portions between the parallel cuts of the spread paste were measured in units of 0.5 mm. Next, an average value of the sizes of the largest and smallest portions between the parallel cuts of the spread paste was determined to be the consistency of the paste.

Next, the consistency and initial setting time of the kneaded material of the dental impression material were evaluated.

[Consistency of Kneaded Material of Dental Impression Material]

Under the condition of 23° C.±2° C., the curing material paste and the base material paste were kneaded to homogeneity by manual kneading at a mass ratio of 1:2, and then 0.5±0.2 ml of the kneaded material of the base material paste and the curing material paste was placed on a glass plate. Next, 30 seconds after kneading the base material paste and the curing material paste was started, weights were loaded so that the total weight of the kneaded material and the glass plate became 500 g. Five seconds after the weights were placed, the weights were removed and the sizes of the largest and smallest portions between the parallel cuts of the spread kneaded material were measured in units of 0.5 mm. Next, an average value of the sizes of the largest and smallest portions between the parallel cuts of the spread kneaded material was determined to be the consistency of the kneaded material.

[Initial Setting Time of Dental Impression Material]

After the curing material paste and the base material paste were kneaded at a mass ratio of 1:2, the initial setting time of the dental impression material was determined in accordance with JIS T 6505:2005, 4.6 Initial setting time Test of Alginate Dental Impression Material.

Next, the compressive strength and Strain-in-compression of the cured body of the dental impression material were evaluated.

[Preparation of Test Piece]

Test pieces were prepared in accordance with JIS T 6505:2005, 6.6.2 Preparation of Test Pieces of alginate impression material for dental use. At this time, the curing material paste and the base material paste were kneaded at a mass ratio of 1:2 and then cured for 90 seconds.

[Compression Strength of Cured Body of Dental Impression Materials]

The compression strength of the cured body of the dental impression material was measured in accordance with JIS T 6505:2005, 6.8 Compression Strength Test of alginate dental impression material.

[Strain-in-Compression of Cured Body of Dental Impression Material]

The strain-in-compression of the cured body of the dental impression material was measured in accordance with JIS T 6505:2005, 6.7 Strain-in-compression Test of alginate dental impression material.

Impressions were taken and the accuracy of the impressions was evaluated using dental impression material and a combination impression material that includes a powdered alginate impression material.

[Preparation of Powdered Alginate Impression Materials]

A powdered alginate impression material was obtained by mixing 15 parts by mass of anhydrous calcium sulfate ($CaSO_4$), 11 parts by mass of sodium alginate I-8 (manufactured by KIMICA Corporation), 65 parts by mass of diatomaceous earth, 3 parts by mass of magnesium hydroxide, 2 parts by mass of zinc oxide, 2 parts by mass of titanium fluoride, and 2 parts by mass of sodium pyrophosphate.

[Accuracy of Impression]

After the base material paste and the curing material paste of the dental impression material were filled into a divided packaging polypropylene cartridge CS 050-02-09 (manufactured by SULZER), the cartridge was sealed by a polyethylene piston (PSA 56-02-SI and PSB 56-02-SI (manufactured by SULZER). Then, using a manual extruder, the base material paste and the curing material paste were extruded and passed through a mixing tip II SS and a mixing tip nozzle (hereinafter, manufactured by GC Corporation) to knead the base material paste and the curing material paste at a mass ratio of 1:2 and inject the kneaded material of the dental impression material into a teeth model in which a cavity is formed.

8.5 g of powdered alginate impression material and 20 ml of distilled water were kneaded and placed on a tray. The kneaded alginate impression material placed on the tray was then pressed against the teeth model in which the kneaded material of the dental impression material was injected to evaluate the accuracy of the impression by the combination impression method.

Evaluation criteria for determining the accuracy of the impression are as follows.

Excellent: The inside of the tooth cavity and the boundary between the teeth and gums are clearly reproduced.

Good: The inside of the tooth cavity is clearly reproduced, but the boundary between the teeth and gums is not clearly reproduced.

Fail: Impression is damaged or the inside of the tooth cavity is not clearly reproduced.

Table 1 indicates the evaluation results of the consistency of the kneaded material of the dental impression material, the initial setting time, the compression strength of the cured body of the dental impression material, strain-in-compression, and the accuracy of the impression.

TABLE 1

| | | Examples | | | | Comparative Examples | | | |
|---|---|---|---|---|---|---|---|---|---|
| | | 1 | 2 | 3 | 4 | 1 | 2 | 3 | 4 |
| Alkali metal salt of alginic acid | K-1G | 8 | | | | | | | |
| | K-3G | | 8 | 6 | | | | | |
| | K-1 | | | | | 8 | | | |
| | K-3 | | | | 8 | | 6 | | |
| | I-8 | | | | | | | 8 | 6 |
| Distilled water | | 91.8 | 91.8 | 91.8 | 91.8 | 91.8 | 91.8 | 91.8 | 91.8 |
| Sodium pyrophosphate | | 0.2 | 0.2 | 0.2 | 0.2 | 0.2 | 0.2 | 0.2 | 0.2 |
| Consistency of base material paste [mm] | | 33.2 | 30.7 | 32.8 | 30.8 | 33.9 | 32.1 | 28.1 | 32.3 |
| Consistency of curing material paste [mm] | | 31.0 | 31.0 | 31.0 | 31.0 | 31.0 | 31.0 | 31.0 | 31.0 |
| Consistency of Kneaded material [mm] | | 40.2 | 38.8 | 39.3 | 40.7 | 37.8 | 40.8 | 35.8 | 39.5 |
| Initial setting time [s] | | 75 | 65 | 70 | 65 | 85 | 70 | 60 | 70 |
| Compressive strength [MPa] | | 0.76 | 1.22 | 0.90 | 0.44 | 0.27 | 0.32 | 0.45 | 0.31 |
| Strain-in-compression [%] | | 14.4 | 15.2 | 15.9 | 19.2 | 19.0 | 18.7 | 20.3 | 20.6 |
| Detail reproduction | | Excellent | Excellent | Excellent | Good | Fail | Fail | Fail | Fail |

From Table 1, it can be seen that the dental impression material of Examples 1 to 4 can obtain a highly accurate impression when combined with a powdered alginate impression material. The dental impression material of Examples 1 to 4 is also more operable than the agar impression material whose fluidity depends on temperature.

In contrast, the dental impression material of Comparative Examples 1, 2, and 4 was damaged because the compressive strength of the cured body was 0.27 to 0.32 MPa.

The consistency of the kneaded material of the base material paste and the curing material paste of the dental impression material of Comparative Example 3 was 35.8 mm, which resulted in low impression accuracy.

The present application is based on and claims priority of Patent Application No. 2019-237346, filed Dec. 26, 2019 with the Japan Patent Office, and the entire contents of Japanese Patent Application No. 2019-237346 are hereby incorporated by reference.

The invention claimed is:

1. A dental impression material for use in a combination impression method, the dental impression material comprising:

a base material paste containing a potassium alginate and water;

a gelling agent; and a curing material paste containing a water-insoluble liquid compound, wherein a consistency of a kneaded material formed of the base material paste and the curing material paste is 36 mm or more, wherein the consistency of the kneaded material being measured by a method including: (1) obtaining the kneaded material by kneading the curing material paste and the base material paste under conditions of 23° C.±2° C. until the kneaded material becomes homogeneous, (2) placing 0.5±0.2 mL of the kneaded material on a glass plate, (3) 30 seconds after starting of kneading of the curing material paste and the base material paste, loading a weight over the glass plate such that a total weight of the glass plate and the kneaded material becomes 500 g, (4) removing the weight 5 seconds after the weight is loaded, and (5) measuring, in units of 0.5 mm, an average value of sizes of largest and smallest portions between parallel cuts of the kneaded material that is spread on the glass plate, the average value being determined as the consistency of the kneaded material, a compressive strength of a cured body is 0.35 MPa or more, a viscosity at 20° C. of 1% by mass of aqueous solution of the potassium alginate in the base material paste is more than 100 mPa·s and less than or equal to 400 mPa·s, a content of the potassium alginate in the base material paste is in a range of 5 mass % to 10 mass %, a content of the water-insoluble liquid compound in the curing material paste is in a range of 15 mass % to 30 mass %.

2. The dental impression material according to claim 1, wherein a strain-in-compression of the cured body is 20% or less.

3. A combination impression material comprising:

the dental impression material of claim 1; and an alginate impression material.

4. The dental impression material according to claim 1, wherein the viscosity at 20° C. of 1% by mass of aqueous solution of the potassium alginate in the base material paste is more than or equal to 200 mPa·s and less than or equal to 400 mPa·s.

* * * * *